United States Patent
Vos

(10) Patent No.: US 9,932,298 B2
(45) Date of Patent: Apr. 3, 2018

(54) PROCESS FOR PRODUCING PENTENENITRILES

(71) Applicant: INVISTA NORTH AMERICA S.A R.L., Wilmington, DE (US)

(72) Inventor: Thomas E. Vos, Beaumont, TX (US)

(73) Assignee: INVISTA NORTH AMERICA S.A R.L., Wilmington, DE (US)

( * ) Notice: Subject to any disclaimer, the term of this patent is extended or adjusted under 35 U.S.C. 154(b) by 162 days.

(21) Appl. No.: 14/649,593

(22) PCT Filed: Dec. 5, 2013

(86) PCT No.: PCT/US2013/073332
§ 371 (c)(1),
(2) Date: Jun. 4, 2015

(87) PCT Pub. No.: WO2014/089303
PCT Pub. Date: Jun. 12, 2014

(65) Prior Publication Data
US 2015/0314279 A1  Nov. 5, 2015

Related U.S. Application Data

(60) Provisional application No. 61/734,543, filed on Dec. 7, 2012.

(51) Int. Cl.
C07C 253/10 (2006.01)
C07C 253/30 (2006.01)
B01J 37/00 (2006.01)
B01J 31/18 (2006.01)
C07C 253/34 (2006.01)

(52) U.S. Cl.
CPC ........... C07C 253/10 (2013.01); B01J 31/185 (2013.01); B01J 37/00 (2013.01); C07C 253/30 (2013.01); C07C 253/34 (2013.01); B01J 2231/322 (2013.01); B01J 2531/847 (2013.01); B01J 2531/90 (2013.01)

(58) Field of Classification Search
CPC .................................................. C07C 253/10
See application file for complete search history.

(56) References Cited

U.S. PATENT DOCUMENTS

| | | |
|---|---|---|
| 3,496,215 A | 2/1970 | Drinkard et al. |
| 3,496,217 A | 2/1970 | Drinkard et al. |
| 3,631,191 A | 12/1971 | Kane et al. |
| 3,655,723 A | 4/1972 | Drinkard |
| 3,766,237 A | 10/1973 | Squire et al. |
| 3,846,461 A | 11/1974 | Shook |
| 3,847,959 A | 11/1974 | Shook et al. |
| 3,903,120 A | 9/1975 | Shook et al. |
| 4,080,374 A | 3/1978 | Corn et al. |
| 4,416,825 A | 11/1983 | Ostermaier |
| 4,705,881 A | 11/1987 | Rapoport |
| 5,512,696 A | 4/1996 | Kreutzer et al. |
| 5,723,641 A | 3/1998 | Tam et al. |
| 6,171,996 B1 | 1/2001 | Garner et al. |
| 7,659,422 B2 | 2/2010 | Foo et al. |
| 7,977,502 B2 | 7/2011 | Foo et al. |
| 8,088,943 B2 | 1/2012 | Foo et al. |
| 2004/0122251 A1* | 6/2004 | Rosier .................. C07C 253/10 558/348 |
| 2008/0242886 A1* | 10/2008 | Bartsch ................. C07C 253/10 558/338 |
| 2009/0182164 A1 | 7/2009 | Foo et al. |
| 2010/0267990 A1 | 10/2010 | Ritter et al. |
| 2011/0196168 A1 | 8/2011 | Ostermaier |
| 2012/0035387 A1 | 2/2012 | Garner et al. |

FOREIGN PATENT DOCUMENTS

| | | |
|---|---|---|
| WO | 2008/008929 A2 | 1/2008 |
| WO | 2011/075494 A1 | 6/2011 |
| WO | 2011/075496 A1 | 6/2011 |
| WO | 2012/033556 A1 | 3/2012 |

OTHER PUBLICATIONS

Mallya, et al.,"Studies on the Basic Carbonates of Nickel",Journal of the Indian Institute of Science, vol. 43, 1961, pp. 65-96.
Rhamdhani, et al."Basic Nickel Carbonate: Part I. Microstructure and Phase Changes during Oxidation and Reduction Processes", Metallurgical and Materials Transactions B, vol. 39B, 2008,pp. 218-233.
International Preliminary Report on Patentability and Written Opinion Received for PCT Application No. PCT/US2013/073332, dated Feb. 25, 2015, 10 pages.
International Search Report Received for PCT Application No. PCT/US2013/073332, dated Mar. 19, 2014, 3 pages.
Tolman, et al.,"Homogeneous Nickel-Catalyzed Olefin Hydrocyanation",Advances in Catalysis, vol. 33, 1985, pp. 1-46.

* cited by examiner

*Primary Examiner* — Joseph R Kosack
(74) *Attorney, Agent, or Firm* — Robert B. Furr, Jr.; Nicholas P. Lanzatella

(57) ABSTRACT

The invention provides methods useful in the industrial scale process for hydrocyanation of butadiene to adiponitrile for recycle of unwanted byproduct 2-methyl-3-butenenitrile (2M3BN) by conversion to process intermediate pentenenitrile. The invention provides a process for generating catalysts useful for carrying out the hydrocyanation of butadiene to adiponitrile, the process comprising contacting the 2M3BN and a solution of a nickel-ligand catalyst in cis-2-pentenenitrile (cis-2PN), trans-2-pentenenitrile (trans-2PN), or a mixture thereof. The improved methods of the invention can provide improved catalyst solubility for bidentate ligands without a requirement for a Lewis acid catalyst promoter such as zinc chloride to be present.

15 Claims, No Drawings

PROCESS FOR PRODUCING PENTENENITRILES

CROSS-REFERENCE TO RELATED APPLICATIONS

This application claims the priority of U.S. provisional application Ser. No. 61/734,543, filed Dec. 7, 2012, the disclosure of which is incorporated herein in its entirety.

FIELD OF THE INVENTION

The invention relates to methods useful in industrial scale processes in the hydrocyanation of unsaturated hydrocarbons such as butadiene, for the production of nylon precursors such as adiponitrile. The invention provides improved catalyst systems and methods for their use in isomerization of 3-methyl-2-butenenitrile to pentenenitriles, useful in the nylon synthesis field.

BACKGROUND

Hydrocyanation catalyst systems useful for the hydrocyanation of ethylenically unsaturated compounds using transition metal complexes with monodentate phosphite ligands are documented in the prior art. See, for example, U.S. Pat. Nos. 3,496,215; 3,631,191; 3,655,723 and 3,766,237, and Tolman et al., Advances in Catalysis, 1985, 33, 1. The hydrocyanation of activated ethylenically unsaturated compounds, such as with conjugated ethylenically unsaturated compounds (e.g., BD and styrene), and strained ethylenically unsaturated compounds (e.g., norbornene) proceed without the use of a Lewis acid promoter, while hydrocyanation of unactivated ethylenically unsaturated compounds, such as 1-octene and 3-pentenenitrile (3PN), generally requires the use of a Lewis acid promoter. Recently, catalyst compositions and processes for the hydrocyanation of monoethylenically unsaturated compounds using zero-valent nickel and bidentate phosphite ligands in the presence of Lewis acid promoters have been described; for example in U.S. Pat. Nos. 5,512,696; 5,723,641; and 6,171,996.

U.S. Pat. No. 3,903,120 describes the preparation of zerovalent nickel complexes of the types $Ni(MZ_3)_4$ (i.e., $ML_4$ type) and $Ni(MZ_3)_2A$ (i.e. $ML_2A$ type); wherein M is P, As or Sb; Z is R or OR, wherein R is an alkyl or aryl radical having up to 18 carbon atoms and may be the same or different, and at least one Z is OR; A is a monoolefinic compound having 2 to 20 carbon atoms; the R radicals of a given $MZ_3$ of $Ni(MZ_3)_2A$ preferably being so chosen that the ligand has a cone angle of at least 130'; are prepared by reacting elemental nickel with the monodentate $MZ_3$ ligand at a temperature in the range of 0° C.-150° C. in the presence of a halogen-containing derivative of the monodentate $MZ_3$ ligand as a catalyst. A more rapid reaction is realized by carrying out the preparation in an organonitrile solvent. In comparison to monodentate phosphorus-containing ligands, bidentate phosphorus-containing ligands generally react more slowly with nickel metals described in the above references. Certain bidentate ligands, such as those that do not readily form $NiL_4$ complexes with nickel metal (i.e., do not form complexes with two moles of bidentate ligand per metal atom), will react more readily in the presence in the presence of Lewis acid promoters, such as $ZnCl_2$, forming higher concentrations of solubilized nickel, as its ligand complex, in the organic reaction milieu.

U.S. Pat. No. 4,416,825 also describes an improved, continuous process for the preparation of hydrocyanation catalysts comprising zerovalent nickel complexes with monodentate organophosphorus compounds (ligands) by controlling the temperature of the reaction relative to the amount of monodentate ligand and conducting the reaction in the presence of a chlorine ion and organic nitrile such as adiponitrile.

There are several processes that can be used to make nickel catalyst complexes with phosphorous-containing ligands. One method is a reaction between nickel bis(1,5-cyclooctadiene) $[NI(COD)_2]$ and a phosphite ligand; however, this process is not very economical because of the high costs of $Ni(COD)_2$. Another process involves the in situ reduction of anhydrous nickel chloride with zinc dust in the presence of the phosphite ligand. For this reaction to be successful, the nickel metal must react with the phosphorous-containing ligand at a sufficient rate to produce the nickel complex.

U.S. Pat. No. 6,171,996 describes zero-valent nickel complexes comprising bidentate phosphite ligands prepared or generated according to techniques well known in the art, as described, for example, in U.S. Pat. Nos. 3,496,217; 3,631,191; 3,846,461; 3,847,959 and 3,903,120. For example, divalent nickel compounds may be combined with a reducing agent, to serve as a source of zero-valent nickel in the reaction. Suitable divalent nickel compounds are said to include compounds of the formula $NiY_2$ where Y is halide, carboxylate, or acetylacetonate. Suitable reducing agents are said to include metal borohydrides, metal aluminum hydrides, metal alkyls, Zn, Fe, Al, Na, or $H_2$. Elemental nickel, preferably nickel powder, when combined with a halogenated catalyst, as described in U.S. Pat. No. 3,903,120 is also a suitable source of zero-valent nickel.

In comparison to monodentate phosphorus-containing ligands, bidentate phosphorus-containing ligands generally react more slowly with nickel metals described in the above references, and generally form metal complexes of the $NiL_2A$ (one mole of bidentate ligand per metal atom, plus unsaturated species A) rather than the $NiL_4$ type (2 moles of bidentate ligand per metal atom).

Many nickel salts can be converted to nickel metal by reduction with hydrogen at elevated temperatures. Potential sources are nickel oxide, nickel formate, nickel oxalate, nickel hydroxide, nickel carbonate, and basic nickel carbonate (BNC). BNC production has been disclosed by R. M. Mallya, et al. in the Journal of the Indian Institute of Science 1961, Vol. 43, pages 44-157 and M. A. Rhamdhani, et al., Metallurgical and Materials Transactions B 2008, Vol. 39B, pages 218-233 and 234-245.

One example of a suitable nickel metal is the INCO type 123 nickel metal powder (Chemical Abstract Service registry number 7440-02-0), derived from the decomposition of nickel carbonyl at elevated temperatures. A method of preparation of a nickel metal suitable for complex formation with phosphite ligand is disclosed in U.S. Published Patent Application No. 2011/0196168. Additional background on hydrocyanation and the adiponitrile (ADN) process is contained in U.S. Pat. No. 8,088,943 B2 and U.S. Pub No: US 2012/0035387 A1.

SUMMARY

The present invention is directed to catalyst compositions comprising relatively high and catalytically effective concentrations of bidentate ligand complexes of nickel in solvent milieu comprising 2-pentenenitriles (2PN) in the absence of Lewis acid promoters, which can be used for hydrocyanation of butadiene and isomerization of 2-methyl- 3-butenenitrile (2M3BN) to pentenenitriles. The invention is also directed to reaction milieu comprising the catalyst systems wherein hydrocyanation of butadiene and isomerization of 2-methyl-3-butenenitrile (2M3BN) to pentenenitriles can occur at usefully low temperatures, such as at temperatures of 80° C. to 140° C., for example within the range of 100° C. to 130° C. The invention is also directed to methods of generating useful concentrations of bidentate nickel-ligand hydrocyanation catalyst in a hydrocyanation reaction milieu, free of Lewis acid promoters such as zinc chloride, for the hydrocyanation of butadiene to pentenenitriles and for isomerization of unwanted butadiene hydrocyanation byproduct 2-methyl-3-butenenitrile (2M3BN) to pentenenitriles. Pentenenitriles can then be carried on as intermediates for further hydrocyanation in the production of adiponitrile (ADN).

The catalyst systems, reaction milieu, and methods, of the present invention comprise use of cis-2-pentenenitrile or trans-2-pentenenitrile, or mixtures thereof, for enhancement of the solubilization of nickel metal by reaction with bidentate ligands as described herein, to form catalytically active nickel-ligand species in organic solution, without a requirement for the presence of Lewis acid promoters such as zinc chloride. The organic solutions in which the nickel-ligand complexes achieve the surprisingly high solubility through the inventive use of 2-pentenenitriles (2PN), or either or both isomeric forms, are suitable as a component of a hydrocyanation reaction milieu comprising butadiene and hydrogen cyanide. For example, effective concentrations of $NiL_2$ species, wherein the two nickel-complexing groups L (ligand) are comprised by a single bidentate phosphorus-containing ligand ($L_2$) molecule per nickel metal atom, can be achieved in the absence of a Lewis acid promoter such as zinc chloride by the presence of 2PN. These catalyst concentrations and their reactivities are suitable for 2M3BN isomerization and hydrocyanation of BD to pentenenitrile, at industrially useful temperatures, achieving reaction rates suitable for industrial-scale production of ADN.

In methods of the invention, use of an improved catalyst preparation method of the invention results in a higher efficiency of converting an unwanted byproduct, 2M3BN, to a pentenenitrile (PN), which can further undergo hydrocyanation reaction to yield adiponitrile. The use of Lewis acid reaction promoters such as $ZnCl_2$ can be avoided. Preparation of the nickel-ligand catalytic process in 2-pentenenitrile, followed by contacting byproduct 2M3BN with the catalyst solution in a hydrocyanation reaction milieu under conditions suitable to bring about hydrocyanation of BD can result in efficient isomerization of the 2M3BN byproduct to useful pentenenitriles, without the presence of Lewis acids.

Accordingly, preparation of the nickel-ligand catalytic system in 2-pentenenitrile, followed by contacting butadiene and hydrogen cyanide with the catalyst solution, can result in efficient hydrocyanation of butadiene to pentenenitriles and 2-methyl-3-butanenitrile without the presence of Lewis acids present from the catalyst preparation reaction.

In various embodiments, the invention provides a method of isomerizing 2-methyl-3-butenenitrile to a pentenenitrile, comprising contacting the 2-methyl-3-butenenitrile and a catalytic nickel-ligand complex, wherein the ligand is a phosphorus-based ligand of formula (III)

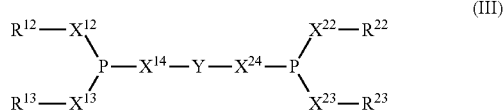
(III)

(wherein the substituent groups are as defined below), in cis-2-pentenenitrile or trans-2-pentenenitrile, without the presence of a Lewis acid such as $ZnCl_2$, under conditions suitable to bring about the isomerization reaction. In various embodiments, the ligand can be a bidentate phosphorus-based ligand. Using methods of the present invention, catalysts preferred for carrying out this isomerization can be more readily prepared.

In various embodiments, the invention provides a process for generating catalysts useful for carrying out the hydrocyanation of butadiene to adiponitrile, wherein an unwanted byproduct of a butadiene hydrocyanation reaction, 2M3BN, is converted in situ to a process intermediate PN that undergoes further hydrocyanation to provide ADN, the process comprising contacting the 2M3BN and a solution of a nickel-ligand catalyst in cis-2PN, trans-2PN, or a mixture thereof. The improved methods of the invention can provide improved catalyst solubility for bidentate ligands without a requirement for a Lewis acid catalyst promoter such as zinc chloride to be present.

DETAILED DESCRIPTION

As used in the specification and the appended claims, the singular forms "a," "an" and "the" include plural referents unless the context clearly dictates otherwise.

The term "about" as used herein, when referring to a numerical value or range, allows for a degree of variability in the value or range, for example, within 10%, or within 5% of a stated value or of a stated limit of a range.

All percent compositions are given as weight-percentages, unless otherwise stated.

If a value of a variable that is necessarily an integer, e.g., the number of carbon atoms in an alkyl group or the number of substituents on a ring, is described as a range, e.g., 0-4, what is meant is that the value can be any integer between 0 and 4 inclusive, i.e., 0, 1, 2, 3, or 4.

The compound or set of compounds, such as are used in the inventive methods, can be any one of any of the combinations and/or sub-combinations of the elements as described herein.

A compound as shown in any of the Examples, or among the exemplary compounds, is provided.

Provisos can apply to any of the disclosed categories wherein any one or more of the other above disclosed categories or species can be excluded from such categories.

Aspects of the present disclosure employ, unless otherwise indicated, techniques of chemistry, and the like, which are within the skill of the art. Such techniques are explained fully in the literature. Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

Phrases such as "under conditions suitable to provide" or "under conditions sufficient to yield" or the like, in the context of methods of synthesis, as used herein refers to reaction conditions, such as time, temperature, solvent, reactant concentrations, and the like, that are within ordinary skill for an experimenter to vary, that provide a useful quantity or yield of a reaction product. It is not necessary that the desired reaction product be the only reaction product or that the starting materials be entirely consumed, provided the desired reaction product can be isolated or otherwise further used.

By "chemically feasible" is meant a bonding arrangement or a compound where the generally understood rules of organic structure are not violated; for example a structure within a definition of a claim that would contain in certain situations a pentavalent carbon atom that would not exist in nature would be understood to not be within the claim. The structures disclosed herein are intended to include only "chemically feasible" structures, and any recited structures that are not chemically feasible, for example in a structure shown with variable atoms or groups, are not intended to be disclosed or claimed herein.

When a substituent is specified to be an atom or atoms of specified identity, "or a bond", a configuration is referred to when the substituent is "a bond" that the groups that are immediately adjacent to the specified substituent are directly connected to each other in a chemically feasible bonding configuration.

All chiral, diastereomeric, racemic forms of a structure are intended, unless a particular stereochemistry or isomeric form is specifically indicated. In several instances though an individual stereoisomer is described among specifically claimed compounds, the stereochemical designation does not imply that alternate isomeric forms are less preferred, undesired, or not claimed. Compounds used in the present invention can include enriched or resolved optical isomers at any or all asymmetric atoms as are apparent from the depictions, at any degree of enrichment. Both racemic and diastereomeric mixtures, as well as the individual optical isomers can be isolated or synthesized so as to be substantially free of their enantiomeric or diastereomeric partners, and these are all within the scope of the invention.

As used herein, the terms "stable compound" and "stable structure" are meant to indicate a compound that is sufficiently robust to survive isolation to a useful degree of purity from a reaction mixture, and formulation into an efficacious therapeutic agent. Only stable compounds are contemplated herein.

An "organic radical" or "organic group", as the term is used herein, refers to a portion or fragment or moiety, capable of bonding to another atom, wherein the group is carbon-based. By "carbon-based" is meant that at least a portion of the group comprises at least one carbon atom, which can be covalently bonded to other atoms capable of covalent bonding such as hydrogen, nitrogen, oxygen, halogen, sulfur, phosphorus, and the like, as is well known in the art.

When a group, e.g., an "alkyl" group or an "aryl" group, is referred to without any limitation on the number of atoms in the group, it is understood that the claim is definite and limited with respect the size of the alkyl group, both by definition; i.e., the size (the number of carbon atoms) possessed by a group such as an alkyl group is a finite number, bounded by the understanding of the person of ordinary skill as to the size of the group as being reasonable for a molecular entity; and by functionality, i.e., the size of the group such as the alkyl group is bounded by the functional properties the group bestows on a molecule containing the group such as solubility in aqueous or organic liquid media. Therefore, a claim reciting an "alkyl" or other chemical group or moiety is definite and bounded.

Standard abbreviations for chemical groups such as are well known in the art can be used herein, and are within ordinary knowledge; e.g., Me=methyl, Et=ethyl, i-Pr=isopropyl, Bu=butyl, t-Bu=tert-butyl, Ph=phenyl, Bn=benzyl, Ac=acetyl, Bz=benzoyl, and the like.

In general, "substituted" refers to an organic group as defined herein in which one or more bonds to a hydrogen atom contained therein are replaced by one or more bonds to a non-hydrogen atom such as, but not limited to, a halogen (i.e., F, Cl, Br, and I); an oxygen atom in groups such as hydroxyl groups, alkoxy groups, aryloxy groups, aralkyloxy groups, oxo(carbonyl) groups, carboxyl groups including carboxylic acids, carboxylates, and carboxylate esters; a sulfur atom in groups such as thiol groups, alkyl and aryl sulfide groups, sulfoxide groups, sulfone groups, sulfonyl groups, and sulfonamide groups; a nitrogen atom in groups such as amines, hydroxylamines, nitriles, nitro groups, N-oxides, hydrazides, azides, and enamines; and other heteroatoms in various other groups. Non-limiting examples of substituents J that can be bonded to a substituted carbon (or other) atom include F, Cl, Br, I, OR', OC(O)N(R')$_2$, CN, NO, NO$_2$, ONO$_2$, azido, CF$_3$, OCF$_3$, R', O (oxo), S (thiono), methylenedioxy, ethylenedioxy, N(R')$_2$, SR', SOR', SO$_2$R', SO$_2$N(R')$_2$, SO$_3$R, C(O)R', C(O)C(O)R', C(O)CH$_2$C(O)R', C(S)R, C(O)OR', OC(O)R', C(O)N(R')$_2$, OC(O)N(R')$_2$, C(S)N(R')$_2$, (CH$_2$)$_{0-2}$N(R')C(O)R', (CH$_2$)$_{0-2}$N(R')N(R')$_2$, N(R')N(R')C(O)R', N(R')N(R')C(O)OR', N(R')N(R')CON(R')$_2$, N(R')SO$_2$R, N(R')SO$_2$N(R')$_2$, N(R')C(O)OR', N(R')C(O)R', N(R')C(S)R', N(R')C(O)N(R')$_2$, N(R')C(S)N(R')$_2$, N(COR')COR', N(OR')R', C(=NH)N(R')$_2$, C(O)N(OR')R', or C(=NOR')R' wherein R' can be hydrogen or a carbon-based moiety, and wherein the carbon-based moiety can itself be further substituted; for example, wherein R' can be hydrogen, alkyl, acyl, cycloalkyl, aryl, aralkyl, heterocyclyl, heteroaryl, or heteroarylalkyl, wherein any alkyl, acyl, cycloalkyl, aryl, aralkyl, heterocyclyl, heteroaryl, or heteroarylalkyl or R' can be independently mono- or multi-substituted with J; or wherein two R' groups bonded to a nitrogen atom or to adjacent nitrogen atoms can together with the nitrogen atom or atoms form a heterocyclyl, which can be mono- or independently multi-substituted with J.

Substituent groups J can independently be halo, nitro, cyano, OR, NR$_2$, or R, or is C(O)OR, C(O)NR$_2$, OC(O)OR, OC(O)NR$_2$, N(R)C(O)OR, N(R)C(O)NR$_2$ or thio/thiono analogs thereof. By "thio/thiono analogs thereof", with respect to a group containing an O, is meant that any or all O atoms in the group can be replaced by an S atom; e.g., for group C(O)OR, a "thio/thiono analog thereof" includes C(S)OR, C(O)SR, and C(S)SR; e.g., for group OC(O)NR$_2$, a "thio/thiono analog thereof" includes SC(O)NR$_2$, OC(S)NR$_2$, and SC(S)NR$_2$; and so forth.

When a substituent is monovalent, such as, for example, F or Cl, it is bonded to the atom it is substituting by a single bond. When a substituent is more than monovalent, such as O, which is divalent, it can be bonded to the atom it is substituting by more than one bond, i.e., a divalent substituent is bonded by a double bond; for example, a C substituted with O forms a carbonyl group, C=O, which can also be written as "CO", "C(O)", or "C(=O)", wherein the C and the O are double bonded. When a carbon atom is substituted with a double-bonded oxygen (=O) group, the oxygen substituent is termed an "oxo" group. When a divalent substituent such as NR is double-bonded to a carbon atom, the resulting C(=NR) group is termed an "imino" group. When a divalent substituent such as S is double-bonded to a carbon atom, the results C(=S) group is termed a "thiocarbonyl" or "thiono" group.

Alternatively, a divalent substituent such as O or S can be connected by two single bonds to two different carbon atoms. For example, O, a divalent substituent, can be bonded to each of two adjacent carbon atoms to provide an epoxide group, or the O can form a bridging ether group, termed an "oxy" group, between adjacent or non-adjacent carbon atoms, for example bridging the 1,4-carbons of a cyclohexyl group to form a [2.2.1]-oxabicyclo system. Further, any substituent can be bonded to a carbon or other atom by a linker, such as $(CH_2)_n$ or $(CR'_2)_n$ wherein n is 1, 2, 3, or more, and each R' is independently selected.

Alkyl groups include straight chain and branched alkyl groups and cycloalkyl groups having from 1 to about 20 carbon atoms, and typically from 1 to 12 carbons or, from 1 to 8 carbon atoms. Examples of straight chain alkyl groups include those with from 1 to 8 carbon atoms such as methyl, ethyl, n-propyl, n-butyl, n-pentyl, n-hexyl, n-heptyl, and n-octyl groups. Examples of branched alkyl groups include, but are not limited to, isopropyl, iso-butyl, sec-butyl, t-butyl, neopentyl, isopentyl, and 2,2-dimethylpropyl groups. As used herein, the term "alkyl" encompasses n-alkyl, isoalkyl, and anteisoalkyl groups as well as other branched chain forms of alkyl. Representative substituted alkyl groups can be substituted one or more times with any of the groups listed above, for example, amino, hydroxy, cyano, carboxy, nitro, thio, alkoxy, and halogen groups.

Cycloalkyl groups are cyclic alkyl groups such as, but not limited to, cyclopropyl, cyclobutyl, cyclopentyl, cyclohexyl, cycloheptyl, and cyclooctyl groups. The cycloalkyl group can have 3 to about 8-12 ring members, or, the number of ring carbon atoms range from 3 to 4, 5, 6, or 7. Cycloalkyl groups further include polycyclic cycloalkyl groups such as, but not limited to, norbornyl, adamantyl, bornyl, camphenyl, isocamphenyl, and carenyl groups, and fused rings such as, but not limited to, decalinyl, and the like. Cycloalkyl groups also include rings that are substituted with straight or branched chain alkyl groups as defined above. Representative substituted cycloalkyl groups can be mono-substituted or substituted more than once, such as, but not limited to, 2,2-, 2,3-, 2,4-2,5- or 2,6-disubstituted cyclohexyl groups or mono-, di- or tri-substituted norbornyl or cycloheptyl groups, which can be substituted with, for example, amino, hydroxy, cyano, carboxy, nitro, thio, alkoxy, and halogen groups. The term "cycloalkenyl" alone or in combination denotes a cyclic alkenyl group.

(Cycloalkyl)alkyl groups, also denoted cycloalkylalkyl, are alkyl groups as defined above in which a hydrogen or carbon bond of the alkyl group is replaced with a bond to a cycloalkyl group as defined above.

The term "alkoxy" refers to an oxygen atom connected to an alkyl group, including a cycloalkyl group, as are defined above. Examples of linear alkoxy groups include but are not limited to methoxy, ethoxy, propoxy, butoxy, pentyloxy, hexyloxy, and the like. Examples of branched alkoxy include but are not limited to isopropoxy, sec-butoxy, tert-butoxy, isopentyloxy, isohexyloxy, and the like. Examples of cyclic alkoxy include but are not limited to cyclopropyloxy, cyclobutyloxy, cyclopentyloxy, cyclohexyloxy, and the like. An alkoxy group can include one to about 12-20 carbon atoms bonded to the oxygen atom, and can further include double or triple bonds, and can also include heteroatoms. For example, an allyloxy group is an alkoxy group within the meaning herein. A methoxyethoxy group is also an alkoxy group within the meaning herein, as is a methylenedioxy group in a context where two adjacent atoms of a structures are substituted therewith.

Aryl groups are cyclic aromatic hydrocarbons that do not contain heteroatoms in the ring. Thus aryl groups include, but are not limited to, phenyl, azulenyl, heptalenyl, biphenyl, indacenyl, fluorenyl, phenanthrenyl, triphenylenyl, pyrenyl, naphthacenyl, chrysenyl, biphenylenyl, anthracenyl, and naphthyl groups. Aryl groups can contain about 6 to about 14 carbons in the ring portions of the groups. Aryl groups can be unsubstituted or substituted, as defined above. Representative substituted aryl groups can be mono-substituted or substituted more than once, such as, but not limited to, 2-, 3-, 4-, 5-, or 6-substituted phenyl or 2-8 substituted naphthyl groups, which can be substituted with carbon or non-carbon groups such as those listed above. Aryl groups can also bear fused rings, such as fused cycloalkyl rings, within the meaning herein. For example, a tetrahydronaphthyl ring is an example of an aryl group within the meaning herein. Accordingly, an aryl ring includes, for example, a partially hydrogenated system, which can be unsubstituted or substituted, and includes one or more aryl rings substituted with groups such as alkyl, alkoxyl, cycloalkyl, cycloalkoxyl, cycloalkylalkyl, cycloalkoxyalkyl, and the like, and also fused with, e.g., a cycloalkyl ring.

A "pentenenitrile" as the term is used herein refers to linear 5-carbon unsaturated nitriles of all possible stereochemistries, and mixtures thereof. Accordingly, hydrocyanation of butadiene (BD) to yield pentenenitrile (PN) is understood to provide one or more pentenenitrile isomers, such as cis or trans 2-pentenenitrile, 3-pentenenitrile, 4-pentenenitrile, or mixtures thereof. Hydrocyanation of BD can also yield the unwanted byproduct 2-methyl-3-butenenitrile (2M3BN). Isomerization of 2M3BN to PN refers to the rearrangement of the branched chain unsaturated nitrile to the linear unsaturated nitrile.

A "ligand" as the term is used herein refers to a neutral phosphorus-containing organic molecule that can complex a metal atom such as nickel to provide a metal-ligand complex. In the case of nickel complexes with ligands of this type, as described further below, the nickel can be complexed by four phosphorus atom ($ML_4$ type complex), wherein the four complexing phosphorus atoms can be made up by four molecules of a monodentate ligand (each ligand molecule thus containing a single metal-complexing phosphorus atom), or by two molecules of a bidentate ligand (each ligand molecule thus containing two each metal-complexing phosphorus atoms). In other complexes, especially with bulky bidentate ligands, the nickel metal atom can only accommodate two complexing phosphorus atoms, but may be able to be bound to another ligand as well, such as an unsaturated compound. These complexes, referred to as $ML_2A$ or $NiL_2A$ (specifically for nickel) complexes, thus comprise a central nickel atom coordinated by the two phosphorus atoms of a single molecule of a bidentate ligand (or two molecules of a monodentate ligand), in addition to another ligand comprising an unsaturated compound (containing a π-bond), such as an unsaturated nitrile (e.g., 3-pentenenitrile, etc.).

Phosphorus-Based Ligand for Hydrocyanation Catalysts

Complexes of nickel metal with phosphorus-based ligands, such as a nickel complexes with a bidentate ligand of formula (V):

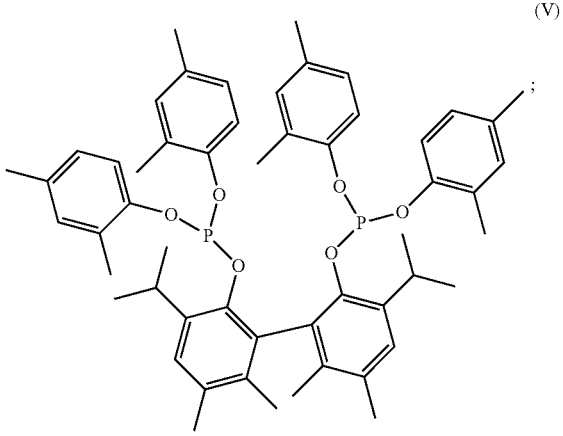

(V)

or of formula (XIII):

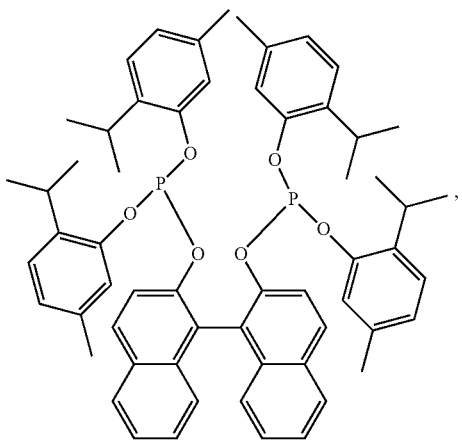

are homogeneous catalysts used in reaction milieu for hydrocyanation reactions, such as the hydrocyanation of butadiene in the manufacture of adiponitrile. Other bidentate ligands can be also used in compositions and methods of the present invention, which are detailed below.

Bidentate ligands often form complexes of the NiL$_2$A (ML$_2$A) type, rather than the NiL$_4$ (ML$_4$) type, which can be due to the steric bulk of the bidentate ligand around the metal atom. In a nickel complex with a ligand of formula (V) or formula (XIII), a ML$_2$A complex comprises one molecule of ligand (V) or ligand (XIII) respectively per nickel metal atom, with additional coordination for the nickel metal atom being provided by unsaturated compound A, which can be an unsaturated nitrile such as a pentenenitrile (PN), (e.g., 3-pentenenitrile, cis or trans), a 2-methyl-3-butenenitrile (2M3BN), or the like, or can be butadiene or another unsaturated organic compound, i.e., as a substrate for a hydrocyanation reaction catalyzed by the metal complex.

Organophosphorus compounds include molecular entities wherein one or more phosphorus atoms is present, and one or more organic radicals or moieties is also present. An organophosphorus compound can further include other elements such as oxygen, halogens, hydrogen, nitrogen, and the like. Some terms in common usage for various classes of organophosphorus compounds, wherein P is a phosphorus atom and R indicates an organic moiety that is bonded via a carbon-phosphorus bond to the phosphorus atom, include "phosphine" (PR$_3$), "phosphine oxide" (P(O)R$_3$), "phosphinite" (P(OR)R$_2$), "phosphonite" (P(OR)$_2$R), "phosphinate" (ROP(O)R$_2$), "phosphite" (P(OR)$_3$), "phosphonate" (RP(O)(OR)$_2$), and "phosphate" (P(O)(OR)$_3$).

A "phosphorus-based ligand" as the term is used herein refers to a ligand containing at least one phosphorus atom, that is suitable for formation of a complex with a transition metal such as nickel, wherein the complex can possess catalytic activity for an organic reaction such as a hydrocyanation reaction of an olefin, such as the hydrocyanation of butadiene to yield pentenenitrile, or the hydrocyanation of pentenenitrile to yield adiponitrile. The term "phosphorus-based" refers to an organic compound that contains at least one phosphorus atom, whether or not it has catalytic activity.

A phosphorus-based ligand containing at least one phosphite ester bond can be a component of a hydrocyanation catalyst, such as when combined with a transition metal, e.g., nickel, as is known in the art. The metal, such as nickel, can be zero-valent, i.e., in metallic form. Reaction of the metal with the ligand can make the complex soluble in certain organic solvents. The ligand can be, for example, a phosphite, a phosphonite, a phosphinite, a phosphine, or a mixed phosphorus-based ligand or a combination of such members, provided the ligand contains at least one hydrolyzable P—O—C bond, wherein P is a phosphorus atom (which additionally bears other substituents), O is an oxygen atom, and C represent an organic radical, such as an aryl group, as described herein.

In general, a phosphorus-based ligand can be monodentate or multidentate, for example, bidentate or tridentate. The term "monodentate" is well known in the art, and means that each molecule of the ligand possesses a single phosphorus atom, which can be bonded to a single metal atom. The term "bidentate" is well known in the art, and means that each molecule of the ligand possesses two phosphorus atoms (e.g., a compound of formula (III), below), and both phosphorus atoms of the ligand can be bonded to a single metal atom. A bidentate ligand is also known in the art as a chelate ligand. The compositions and methods of the present invention relate to nickel complexes with bidentate ligands of the ML$_2$A type.

As used herein, the term "mixed phosphorus-based ligand" means a phosphorus-based ligand comprising at least one combination selected from the group consisting of a phosphite-phosphonite, a phosphite-phosphinite, a phosphite-phosphine, a phosphonite-phosphinite, a phosphonite-phosphine, and a phosphinite-phosphine or a combination of such members, provided that there is at least one P—O—C bond, wherein P is a phosphorus atom, O is an oxygen atom, and C represent an organic radical, such as an aryl group, that is subject to hydrolysis under acid catalysis.

Suitable phosphorus-based ligands for the transition metal, e.g., nickel, complex, can be selected from the group consisting of bidentate ligands of formula (III)

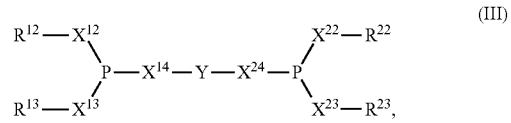

wherein $X^{12}$, $X^{13}$, $X^{14}$, $X^{22}$, $X^{23}$, and $X^{24}$, each independently is oxygen or a bond, provided that at least one of $X^{12}$, $X^{13}$, $X^{14}$, $X^{22}$, $X^{23}$, or $X^{24}$ is oxygen;

$R^{12}$, $R^{13}$, $R^{22}$, and $R^{23}$, each independently is (C1-C10) alkyl, (C3-C10)cycloalkyl, (C3-C10)cycloalkyl(C1-C10) alkyl, (C6-C20)aryl, or (C6-C20)aryl(C1-C10)alkyl, wherein for any (C6-C20)aryl or (C6-C20)aryl(C1-C10) alkyl of $R^{12}$, $R^{13}$, $R^{22}$, or $R^{23}$, each ring thereof is unsubstituted or is substituted with 1-4 substituents independently selected from the group consisting of (C1-C10)alkyl, (C3-C10)cycloalkyl, (C1-C10)alkoxy, (C3-C10)cycloalkoxy, (C3-C10)cycloalkyl(C1-C10)alkyl, (C3-C10)cycloalkoxy (C1-C10)alkyl, (C3-C10)cycloalkyl(C1-C10)alkoxy, (C3-C10)cycloalkoxy(C1-C10)alkoxy, (C6-C20)aryl, and (C6-C20)aryl(C1-C10)alkyl; or, optionally, one or more of pairs $R^{12}$ and $R^{13}$ or $R^{22}$ and $R^{23}$ are mutually directly bonded, such that the $R^{12}X^{12}$ and $R^{13}X^{13}$ groups, or the $R^{22}X^{22}$ and $R^{23}X^{23}$ groups, or both, together with the respective phosphorus atom to which each pair of groups is bonded, forms a respective ring; and, Y is an (C6-C20)arylene group, wherein each ring thereof is independently unsubstituted or is substituted with 1-4 (C1-C10)alkyl, (C3-C10)cycloalkyl, (C1-C10)alkoxy, (C3-C10)cycloalkoxy, (C3-C10)cycloalkyl(C1-C10)alkyl, (C3-C10)cycloalkoxy(C1-C10)alkyl, (C3-C10)cycloalkyl(C1-C10)alkoxy, (C3-C10)cycloalkoxy(C1-C10)alkoxy, (C6-C20)aryl, (C6-C20)aryl(C1-C10)alkyl, fluorine, chlorine, bromine, or (C1-C10)haloalkyl.

An example of a bidentate phosphite ligand that is useful in the present process, i.e., a compound of formula (III), above, is a ligand having formula (V), shown below:

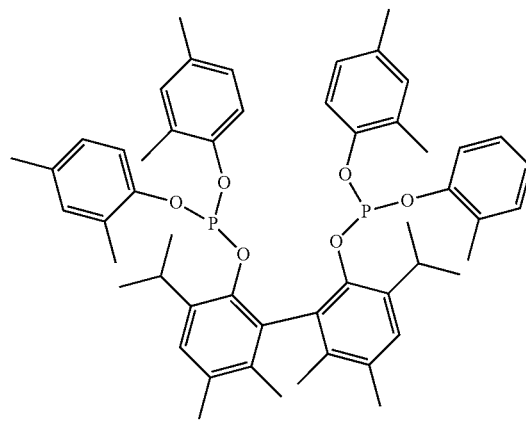

(V)

Another example is a ligand of formula (XIII):

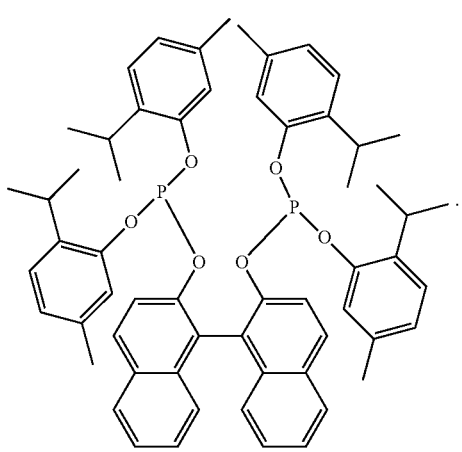

(XIII)

The use of these ligands is described in greater detail below.

Further examples of bidentate phosphite ligands that are useful in the present process include those having the formulas (VI) to (IX), shown below wherein for each formula, $R^{17}$ can selected from the group consisting of methyl, ethyl and isopropyl, and $R^{18}$ and $R^{19}$ can be independently selected from H and methyl. Or, each of $R^{17}$, $R^{18}$, and $R^{19}$ can independently be a higher alkyl, cycloalkyl, alkoxyl, or cycloalkoxyl.

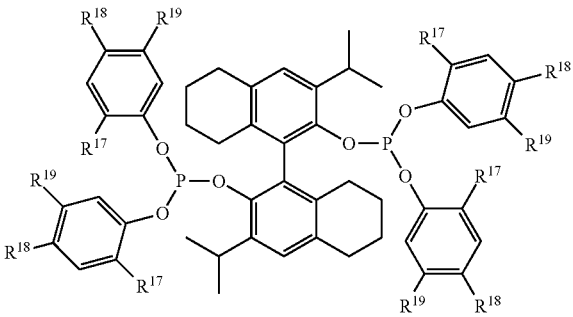

(VI)

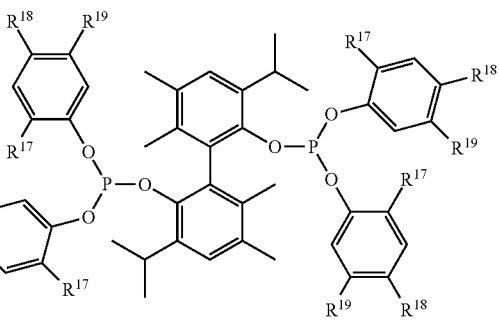

(VII)

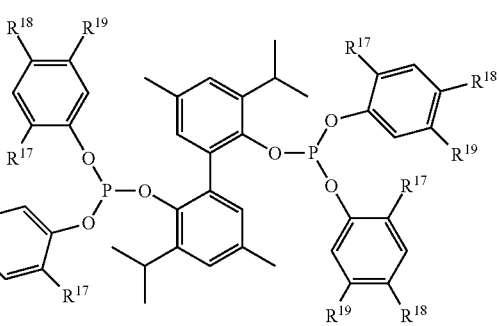

(VIII)

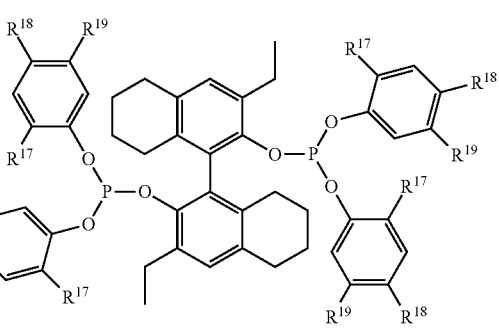

(IX)

Additional examples of bidentate phosphite ligands that are useful in the present process include a ligand selected from a member of the group represented by formulas (X) and (XI), in which all like reference characters have the same meaning, except as further explicitly limited:

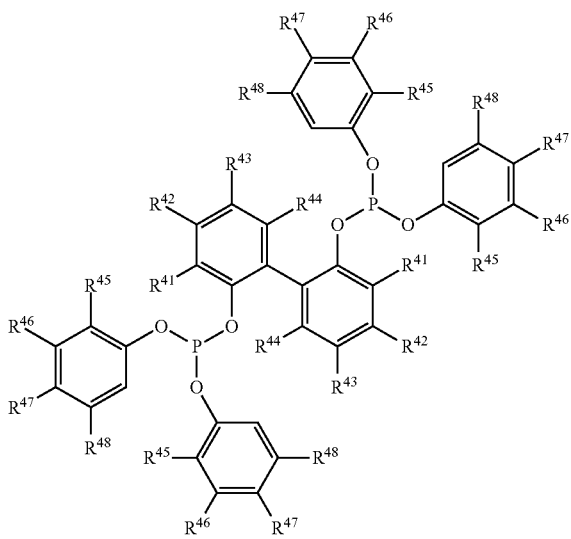

(X)

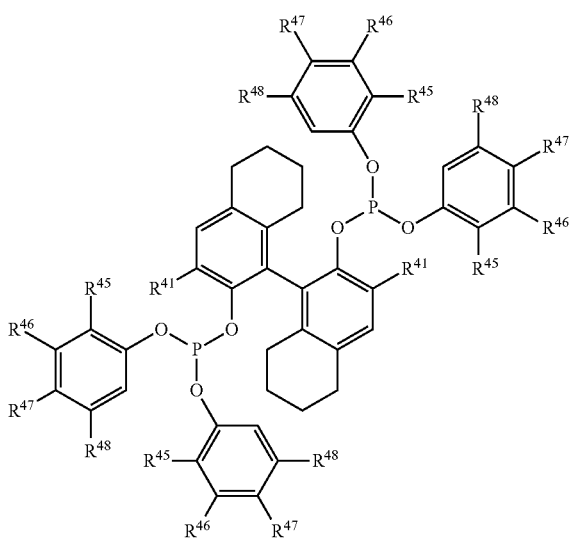

(XI)

wherein $R^{41}$ and $R^{45}$ can be independently selected from the group consisting of C1-C10 alkyl, C3-C10 cycloalkyl, C1-C10 alkoxyl, and C3-C10 cycloalkoxyl, and each of $R^{42}$, $R^{43}$, $R^{44}$, $R^{46}$, $R^{47}$ and $R^{48}$ is independently selected from the group consisting of H, C1-C10 alkyl and C3-C10 cycloalkyl.

For example, the bidentate phosphite ligand can be represented by formula (X) or formula (XI), wherein
$R^{41}$ is methyl, ethyl, isopropyl or cyclopentyl;
$R^{42}$ is H or methyl;
$R^{43}$ is H or C1-C10 alkyl, C3-C10 cycloalkyl, C1-C10 alkoxyl, or C3-C10 cycloalkoxyl;
$R^{44}$ is H or methyl;
$R^{45}$ is methyl, ethyl or isopropyl; and
$R^{46}$, $R^{47}$ and $R^{48}$ are each independently selected from the group consisting of H, C1-C10 alkyl, C3-C10 cycloalkyl, C1-C10 alkoxyl, and C3-C10 cycloalkoxyl.

For example, the bidentate phosphite ligand can be represented by formula (X) or (XI), wherein
$R^{41}$, $R^{44}$, and $R^{45}$ are methyl;
$R^{42}$, $R^{46}$, $R^{47}$ and $R^{48}$ are H; and, $R^{43}$ is a C1-C10 alkyl, C3-C10 cycloalkyl, C1-C10 alkoxyl, or C3-C10 cycloalkoxyl;
or, by the formula (X) or (XI), wherein
$R^{41}$ is isopropyl;
$R^{42}$ is H;
$R^{43}$ is C1-C10 alkyl, C3-C10 cycloalkyl, C1-C10 alkoxyl, or C3-C10 cycloalkoxyl;
$R^{44}$ is H or methyl;
$R^{45}$ is methyl or ethyl;
$R^{46}$ and $R^{48}$ are each independently H or methyl; and
$R^{47}$ is H, methyl or t-butyl.

Alternatively, the bidentate phosphite ligand can be represented by formula (X) or (XI), wherein
$R^{41}$ is isopropyl or cyclopentyl;
$R^{45}$ is methyl or isopropyl; and
$R^{46}$, $R^{47}$, and $R^{48}$ are H.

As yet another example, the bidentate phosphite ligand can be represented by Formula (X) or (XI), wherein $R^{41}$ is isopropyl; $R^{42}$, $R^{46}$, and $R^{48}$ are H; and $R^{43}$, $R^{44}$, $R^{45}$, and $R^{47}$ are methyl.

As another example, the ligand of formula (III) can be of formula (XII):

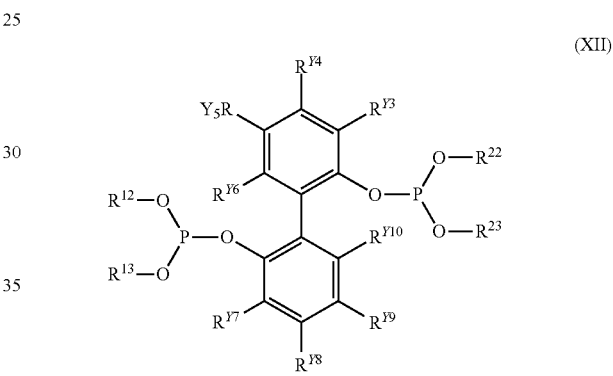

(XII)

wherein each of $R^{12}$, $R^{13}$, $R^{22}$ and $R^{23}$ is independently an unsubstituted or a substituted monovalent aryl, and each of $R^{Y3}$-$R^{Y10}$ is independently selected from the group consisting of hydrogen, (C1-C10) alkyl, and (C1-C10)alkoxy; or wherein two adjacent groups comprising any of $R^{Y3}$-$R^{Y10}$ together form an optionally substituted fused aryl ring. By a "monovalent aryl" group is meant an aryl group, which can be otherwise unsubstituted or substituted, bonded not more than one phosphite group. By an "optionally substituted fused aryl ring" is meant that any adjacent pair of $R^{Y3}$-$R^{Y10}$ can, together with the atoms of the ring to which they are bonded, themselves form another aryl ring which can be unsubstituted or substituted.

More specifically, for example, for a ligand of formula (XII), $R^{12}$, $R^{13}$, $R^{22}$, and $R^{23}$ are each independently phenyl substituted at a respective single ortho-position with a (C1-C10)alkyl or (C1-C10)alkoxy, wherein respective meta- and para-positions of the $R^{12}$, $R^{13}$, $R^{22}$, and $R^{23}$ phenyls can each independently be unsubstituted or be independently substituted with (C1-C10)alkyl, (C3-C10)cycloalkyl, (C1-C10)alkoxy, (C3-C10)cycloalkoxy, (C3-C10)cycloalkyl(C1-C10)alkyl, (C3-C10)cycloalkoxy(C1-C10)alkyl, (C3-C10)cycloalkyl(C1-C10)alkoxy, or (C3-C10)cycloalkoxy(C1-C10)alkoxy;
$R^{Y6}$ and $R^{Y10}$ are independently (C1-C10)alkyl or (C1-C10)alkoxy, and $R^{Y3}$, $R^{Y4}$, $R^{Y5}$, $R^{Y7}$, $R^{Y8}$, and $R^{Y9}$, are independently H, (C1-C10)alkyl, or (C1-C10)alkoxy, provided that at least one of $R^{Y3}$, $R^{Y4}$, or $R^{Y5}$, and at least one of $R^{Y7}$, $R^{Y8}$, or $R^{Y10}$, is (C1-C10)alkyl or (C1-C10)alkoxy.

It will be recognized that Formulas (V) to (XIII) are two-dimensional representations of three-dimensional molecules and that rotation about chemical bonds can occur in the molecules to give configurations differing from those shown. For example, rotation about the carbon-carbon bond between the 2- and 2'-positions of the biphenyl, octahydrobinaphthyl, and or binaphthyl bridging groups of Formulas (V) to (XIII), respectively, can bring the two phosphorus atoms of each Formula in closer proximity to one another and can allow the phosphite ligand to bind to nickel in a bidentate fashion. In addition, use of an optically active moiety such as sec-butyl for $R^{41}$ can result in optically active catalysts.

Hydrocyanation of Butadiene

The hydrocyanation of BD to yield ADN directly or indirectly through isomerization and/or additional hydrocyanation of intermediates with modern phosphorus-containing catalysts set forth below is well known in the art as evidenced by U.S. Pat. Nos. 7,977,502; and 7,659,422 and U.S. Published Applications 2009/0182164 and 2010/0267990. Various modifications can be used alone or in combination to achieve the desired efficiency with the selected components of the reaction. Thus, separation steps, temperatures, refining, distillation, isomerization zones, pressures, elimination of constituents along the pathway, column sizes and configurations, stream velocities, recycling, and other process variables can be adjusted to modify the overall ADN production as required.

The catalyst composition can be dissolved in a solvent that is non-reactive toward, and miscible with, the hydrocyanation reaction mixture. Suitable solvents include, for example, aliphatic and aromatic hydrocarbons with 1 to 10 carbon atoms, and nitrile solvents such as acetonitrile. Alternatively, 3PN, a mixture of isomeric pentenenitriles, a mixture of isomeric methylbutenenitriles, a mixture of isomeric pentenenitriles and isomeric methylbutenenitriles, or the reaction product from a previous reaction campaign, can be used to dissolve to the catalyst composition.

The HCN-containing feed, the BD-containing feed, and the catalyst composition are contacted in a reaction zone which can be contained in any suitable equipment known to one skilled in the art. One or more pieces of conventional equipment can be used to provide the reaction zone, for example continuous stirred-tank reactors, loop-type bubble column reactors, gas circulation reactors, bubble column reactors, tubular reactors, or combinations thereof, optionally with apparatus for removing at least a portion of the heat of reaction.

The reaction temperature is typically maintained within the range of about 80° C. to about 140° C., for example within the range of about 100° C. to about 130° C. Generally, the reaction pressure should be sufficient to maintain the reagents in the liquid state, with such pressure at least, in part, a function of the amount of unreacted BD present in the reaction mixture.

Though the invention is not limited by an upper limit of pressure, for practical purposes the pressure generally ranges from about 15 psia to about 300 psia (about 103 kPa to about 30 2068 kPa).

HCN, substantially free of carbon monoxide, oxygen, ammonia, and water can be introduced to the reaction as a vapor, liquid, or mixtures thereof. As an alternative, cyanohydrins can be used as the source of HCN. See, for example, U.S. Pat. No. 3,655,723.

The molar ratio of the HCN in the feed to the BD in the feed is in the range of about 0.90:1.00 to about 1.04:1.00, for example in the range of about 0.92:1.00 to about 0.98:1.00.

This range of molar ratios can be advantageous over those with a significantly larger excess of BD to HCN in that there can be less unreacted BD to recover and recycle to the process, and yield losses to 2-methylglutaronitrile (MGN) and to BD dimers, oligomers, and related species can be reduced. The molar ratio of the zero-valent nickel in the feed to the BD in the feed is in the range of about 0.00005:1.00 to about 0.0050:1.00, for example in the range about 0.0001:1.00 to about 0.0010:1.00.

The residence time in the reaction zone (for example, the time necessary for the combined feeds to displace one reactor so volume in a continuous-stirred-tank-reactor (CSTR) is typically determined by the desire to maintain the 2M3BN concentration below about 15 weight percent of the total mass of the reaction mixture, for example at or below about 10 weight percent of the total mass of the reaction mixture, and is also related to the catalyst concentration and reaction temperature. Generally residence times will be in the range of about 0.5 to about 15 hours, for example in the range of about 1 to about 10 hours.

Dinitriles can be produced in the first reaction zone by the reaction of 3-pentenenitrile (3PN) or 2-methyl-3-butenenitrile (2M3BN) with HCN. Lewis acids are capable of promoting the formation of dinitriles in the first reaction zone. Lewis acids are preferably not introduced into the first reaction zone in detectable amounts. However, a detectable amount of a Lewis acid can be introduced into the first reaction zone, provided that dinitrile formation is minimized. For example, a detectable amount of a Lewis acid can be introduced into the first reaction zone, provided that the amount of dinitriles produced, when none of the Lewis acid is introduced into the first reaction zone, is not increased by more than 5 wt %.

Isomerization of 2-methyl-3-butenenitrile to pentenenitrile

Reactions which take place in the first reaction zone, for hydrocyanating 1,3-butadiene to a mixture of pentenenitriles and the undesired byproduct 2-methyl-3-butenenitrile, and in the second reaction zone, for isomerizing 2-methyl-3-butenenitrile to pentenenitriles, preferably take place in the absence or substantial absence of a Lewis acid promoter such as $ZnCl_2$.

Unlike using monodentate ligands to make $NiL_4$ type complexes, some bidentate ligands need to have $ZnCl_2$ or small monodentate ligands to cause the nickel to form the complex and go into solution in the solvent medium, which can include alkenenitriles. An unexpected discovery of the present invention is that use of different pentenenitrile isomers, e.g., cis and trans 2-penetenenitriles, impacts on the ability to achieve nickel catalyst solution, which is better suited for hydrocyanating BD and isomerization of 2M3BN, without the requirement for a Lewis acid promoter.

Lewis acid promoters represent an extra cost and a recycling challenge that is preferably avoided, provided the correct reactions occur with suitably high efficiency. See, for example, U.S. Pat. No. 4,080,374, (Corn, et al.), and U.S. Pat. No. 4,705,881 (Rapoport, et al.), describing zinc chloride as a catalyst promoter. See Scheme 1, below. Their elimination from the process can provide substantial process cost savings.

Scheme 1: Hydrocyanation of Butadiene and Isomerization of 2-methyl-3-butenenitrile

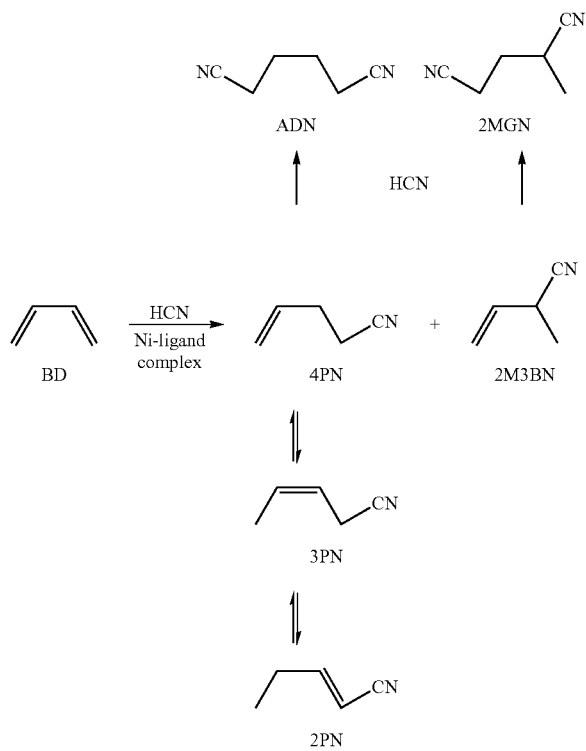

Butadiene can react with hydrogen cyanide in the presence of a suitable nickel-ligand complex to yield two isomeric HCN double bond addition products; respectively resulting from addition of the cyanide group to a primary carbon atom and from addition of the cyanide group to a secondary carbon atom. The primary carbon addition product, 4-pentenenitrile (4PN) can undergo double bond isomerization to 3-pentenenitriles (3PN-cis and trans) and 2-pentenenitriles (2PN-cis and trans) under the reaction conditions, and is structurally set up to yield the desired product adiponitrile upon the second HCN addition reaction. The secondary carbon addition product, 2-methyl-3-butenenitrile (2M3BN), however, upon addition of a second HCN molecule yields the undesirable 2-methylglutaronitrile (2MGN), which is unsuitable for the further reactions of ADN in the production of adipic acid, caprolactam, or 1,6-diaminohexane.

However, if the 2M3BN can be isomerized back to a PN isomer, losses due to the undesirable side-reaction can be diminished.

3-pentenenitrile produced in the first and second reaction zones can be reacted with hydrogen cyanide to produce dinitriles comprising adiponitrile in a third reaction zone downstream of the first and second reaction zones. A catalyst system comprising a Lewis acid promoter can flow through the third reaction zone along with reactants and products, which is undesirable. Preferably, none of the Lewis acid promoter which flows from the third reaction zone flows into the first reaction zone. By elimination of the presence of the Lewis acid promoter, this problem can be avoided.

The inventor herein has unexpectedly discovered that by use of particular unsaturated nitriles, the bidentate ligand catalyst could be generated in the solvent system at sufficient concentration to carry out the industrial scale process, without a requirement for the presence of Lewis acid promoter. Accordingly, the catalyst systems and reaction milieu of the present invention are thereby preferred for hydrocyanation of 1,3-butadiene and for isomerization of 2-methyl-3-butenenitrile to pentenenitriles.

Use of Nitrile Solvents in Isomerization Reactions

Ni metal suitable for nickel catalyst preparation was prepared from basic nickel carbonates as described in International Application Number PCT/US10/60381, International Application Number PCT/US10/60388, International Application Number PCT/US11/40193.

In U.S. Patent Application Publication Number 2011/0196168, incorporated by reference herein in its entirety, it is described that in formation of a solution of a nickel complex with a bidentate phosphorus-based ligand (e.g., a triarylphosphite such as ligand (V)), the reaction mixture may further comprise an organonitrile selected from one or more members of the group consisting of 2-pentenenitrile, 3-pentenenitrile, 4-pentenenitrile, 2-methyl-3-butenenitrile, 2-methyl-2-bytenenitrile, adiponitrile, 2-methylglutaronitrile, and ethylsuccinotrile. The '168 application further discloses that making the nickel complex or nickel complexes from the reaction of monodentate and bidentate ligands with the nickel-containing solids of this invention may be performed as described in therein; for example, a 5 wt % solution of a bidentate phosphorus-containing ligand in pentenenitrile solvent further comprising a Lewis acid like $ZnCl_2$ (0.5 to 2.5 moles Lewis acid per mole bidentate phosphorus-containing ligand) can be contacted with the nickel-containing solid of the invention (for example, 4.0 wt % nickel-containing solid). Temperatures between 60° C. and 80° C. gave acceptable reaction rates. The '168 application discloses that additional $ZnCl_2$ would promote higher nickel catalyst concentrations, but this is not preferred, due to higher cost of $ZnCl_2$ used in the process for pentenenitrile hydrocyanation, as the $ZnCl_2$ is not recovered for recycling.

In an improvement upon this procedure, the present invention provides methods and compositions wherein specific pentenenitrile solvents are used, and 2M3BN isomerization to PNs can be accomplished in the absence of a Lewis acid from the catalyst-containing homogeneous composition. It has unexpectedly been found by the inventor herein that use of cis-2-pentenenitrile (cis-2PN) and/or trans-2-pentenenitrile (trans-2PN), or mixtures thereof, as the solvent for a catalytic complex of nickel with ligand (V), even in the absence of $ZnCl_2$, provides for a highly efficient isomerization of 2M3BN to pentenenitrile; a more effective isomerization of the unwanted 2M3BN isomer to a useful PN is achieved in cis-2PN and/or trans-2PN than that is achieved in 3PN, even in the presence of the promoter $ZnCl_2$.

Diphosphite ligand (V) was prepared according to the procedure published in International Application Number PCT/US10/60381, International Application Number PCT/US10/60388, International Application Number PCT/US11/

40193. The method of formation also can result in relatively minor quantities of monodentate ligands (7) and (8), shown below, being formed.

a bidentate ligand

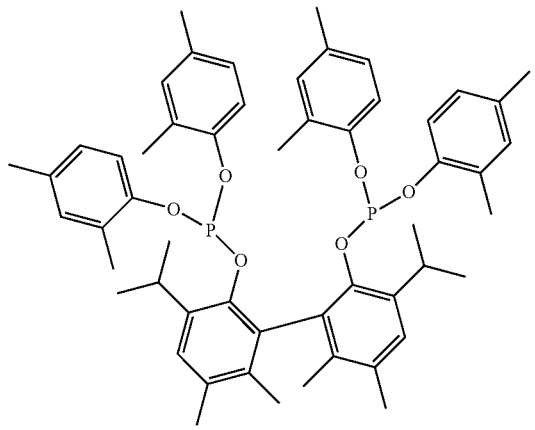

(V)

monodenate ligands

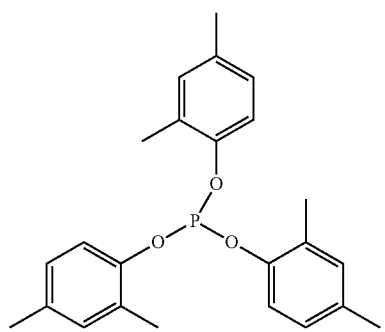

(7)

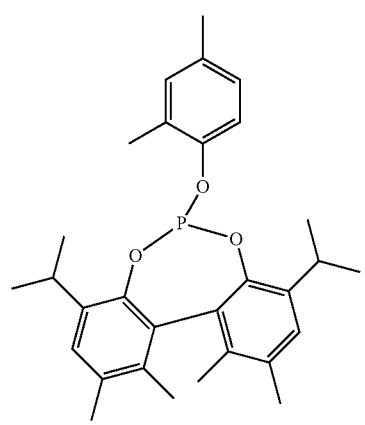

(8)

Typically, in the industrial hydrocyanation process, the bidentate ligand such as (V) can be used in the presence of minor impurity levels of monodentate ligands such as (7) and (8) that arise from equilibration among the phosphate esters. As is apparent, the monodentate ligands (7) and (8) contain the same phenolic moieties as does (V). The ligand (V) solution can be a mixture in toluene and/or cyclohexane with the major component (exclusive of solvent) being (V), but also including (7), (8), and hydrolysis products of (V), (7), or (8), and other products derived from the compounds used for (V) synthesis. The composition of the bidentate ligand (V) in cyclohexane used in the experimental studies herein is provided in Table 1.

TABLE 1

| Composition of Ligand (V) | | | |
|---|---|---|---|
| | % wt by HPLC analysis | | |
| | (7) | (8) | (V) |
| V solution | 4.4% | 2.4% | 34.5% |

Diphosphite ligand (XIII) was prepared in a similar manner as diposphite ligand (V) according to the procedure published in International Application Number PCT/US10/60381, International Application Number PCT/US10/60388, International Application Number PCT/US11/40193. The method of formation also can result in relatively minor quantities of monodentate ligands (9) and (10), shown below, being formed.

a bidentate ligand

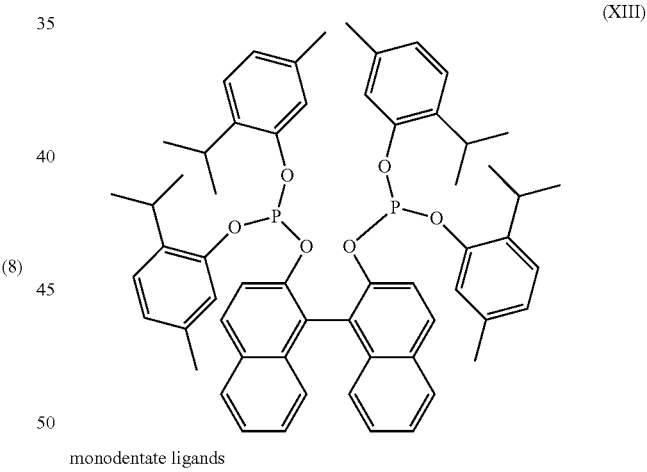

(XIII)

monodentate ligands

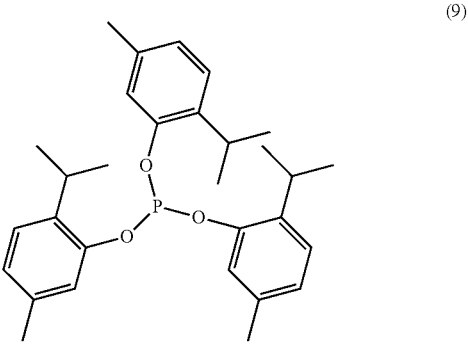

(9)

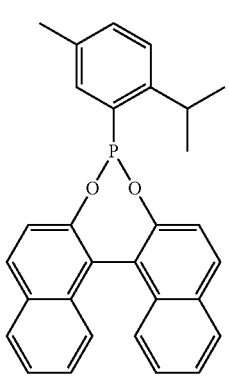

(10)

Studies were conducted to investigate the effectiveness of 2M3BN isomerization in compositions detailed in the Examples section. Results are shown in Table 3, below.

Table 2 shows the levels of solubilized nickel catalysts that were achieved in each of the Examples 1-9.

TABLE 2

Nickel Content of solubilized Ni-ligand (V) and Ni-ligand (XIII) complexes

| | Ni $ppm_w$ soluble in solution |
|---|---|
| Example 1 | 4293 |
| Example 2 | 390 |
| Example 3 | 2716 |
| Example 4 | 3526 |
| Example 5 | 1797 |
| Example 6 | 840 |
| Example 7 | 464 |
| Example 8 | 566 |
| Example 9 | 337 |

Examples 1-5 relate to solubilization of nickel by ligand (V) in various solvent and presence or absence of zinc chloride, and examples 6-9 are comparable examples using ligand (XIII).

Example 1, below, describes the preparation of a catalytic solution of Ni-ligand(V) catalyst in 3PN with zinc chloride (ZnCl$_2$) and its use in isomerization of 2M3BN to a PN. Example 2 describes the preparation of a catalytic solution of Ni-ligand(V) catalyst in 3PN without zinc chloride, and its use in isomerization of 2M3BN to a PN. Example 3 describes the preparation of a catalytic solution of Ni-ligand (V) catalyst in cis-2-PN without zinc chloride, and its use in isomerization of 2M3BN to a PN. Example 4 describes the preparation of the solution of the catalytic Ni-ligand(V) catalyst in trans-2-PN with zinc chloride; example 5 describes a comparable solution preparation but without zinc chloride; examples 6, 7, 8, and 9 describes a comparable solution preparation but using ligand (XIII), in 2-PN with and without zinc chloride, and in 3-PN with and without zinc chloride.

As can be seen, the level of nickel catalyst dissolving as a ligand complex with the ligand of formula (V) in the reaction milieu when 3-PN is the solvent is strongly affected by the presence of zinc chloride; about 10× more nickel is solubilized. When 2-PN is used, however, comparable levels of nickel solubilization are observed with and without the presence of the zinc chloride promoter; see examples 3 versus 4 and 6 versus 5; the difference between dissolved nickel levels is much less dependent upon the presence of zinc chloride.

Dissolution of the nickel complex of ligand (XIII), as seen in examples 6-9, is less affected by the difference between 2-PN (example 6 and 7) and 3-PN (examples 8 and 9) in the presence versus absence of zinc chloride, although it is seen that higher levels of solubilized nickel are obtained using 2-PN as solvent.

Table 3 provides the results of 2M3BN isomerization reactions under the conditions detailed in the Examples 1-9 for the three catalyst solvent systems investigated, i.e., 3PN with and without ZnCl$_2$ promoter, and cis- and trans-2PN with and without ZnCl$_2$ promoter, at time 0 and time 5 hours. Examples 1-5 relate to use of the ligand of formula (V) and examples 6-9 relate to use of the ligand of formula (XIII).

TABLE 3

Isomerization of 2-methyl-3-butenenitrile to pentenenitriles

| | | % wt by GC | | | | % 2M3BN |
|---|---|---|---|---|---|---|
| | Time | 2M3BN | 3PN | 4PN | 2PN | conversion |
| Example 1 | 0 h | 79.1% | 10.1% | 0.1% | 1.6% | |
| Example 1 | 5 h | 47.3% | 41.5% | 0.1% | 1.6% | 40% |
| Example 2 | 0 h | 79.1% | 10.1% | 0.1% | 1.7% | |
| Example 2 | 5 h | 57.6% | 31.2% | 0.1% | 1.7% | 27% |
| Example 3 | 0 h | 78.9% | 3.4% | 0.0% | 8.6% | |
| Example 3 | 5 h | 9.9% | 72.3% | 0.0% | 8.6% | 87% |
| Example 4 | 0 h | 80.9% | 3.3% | 0.1% | 8.7% | |
| Example 4 | 5 h | 65.1% | 18.3% | 0.1% | 8.7% | 19% |
| Example 5 | 0 h | 79.0% | 3.2% | 0.1% | 8.7% | |
| Example 5 | 5 h | 34.8% | 48.0% | 0.1% | 8.7% | 56% |
| Example 6 | 0 h | 80.6% | 3.3% | 0.0% | 8.7% | |
| Example 6 | 5 h | 77.8% | 5.1% | 0.0% | 8.7% | 3% |
| Example 7 | 0 h | 80.0% | 3.2% | 0.1% | 9.0% | |
| Example 7 | 5 h | 74.1% | 5.4% | 0.1% | 8.7% | 7% |
| Example 8 | 0 h | 79.2% | 10.3% | 0.1% | 1.6% | |
| Example 8 | 5 h | 79.7% | 11.3% | 0.1% | 1.6% | 0% |
| Example 9 | 0 h | 79.6% | 10.4% | 0.1% | 1.6% | |
| Example 9 | 5 h | 79.0% | 11.4% | 0.1% | 1.6% | 1% |

3PN refers to both trans-3-pentenenitrile and cis-3-pentenenitrile. 2PN refers to cis-2-pentenenitrile and trans-2-pentenenitrile and 2M3BN refers to 2-methyl-3-butenenitrile.

The data presented in Table 3 show that catalyst solutions made from Ligand (V) in cis-2-pentenenitrile or trans-2-pentenenitrile are more reactive for isomerization 2-methyl-3-butenenitrile to 3-pentenenitrile and 4-pentenenitrile. Examples 1 and 2 show the extent of isomerization of 2M3BN in 3-PN with and without zinc chloride. The results are roughly comparable at 5 hours. Examples 3 and 5 show the extent of 2M3BN isomerization in cis- and trans-2-PN without zinc chloride, and example 4 adds zinc chloride to the trans-2-PN. As can be seen in Table 3, a greater extent of isomerization of 2M3BN is observed using either isomer of 2-PN compared to using 3-PN as solvent. However, addition of zinc chloride to the 2-PN reduces the amount of 2M3BN isomerization observed. These results show that 2-PN, of either isomer, in the absence of a Lewis acid promoter such as zinc chloride, is a superior reaction milieu for isomerization of 2M3BN using a nickel complex of ligand (V). As can be seen further, ligand (XIII) in nickel-complexed form is a less effective isomerization catalyst under all conditions.

Catalyst preparation with 3-pentenenitrile and 4-pentenenitrile without zinc chloride resulted in a very dilute nickel catalyst concentration that does not isomerize 2-methyl-3-butenenitrile as well as cis-2-pentenenitrile or trans 2-pentenenitrile catalyst solution. Isomerization rates and catalyst preparation conditions change depending on the type of 5 carbon unsaturated nitriles isomer used in the catalyst preparation reaction.

As Table 2 indicates, the level of solubilized nickel-ligand catalyst is the highest in Example 1; in Example 2 about 90% less dissolved; and in Example 3, about 40% less dissolved compared to Example 1. However, Example 3 showed more the twice the amount of 2M3BN isomerization to PNs than did Example 1. Example 4, about 20% less dissolved compared to Example 1 and about 50% the amount of 2M3BN isomerization to PNs than Example 1. Example 5, about 60% less dissolved compare to Example 1 and about 1.5 times the isomerization of 2M3BN. With the second bidentate ligand (XIII) set shown in examples 6-9, the same trend holds albeit much slower initial rates in that the zinc chloride slows down the isomerization reaction rate and there is a faster reaction rate with the catalyst made in 2-pentenenitrile. Under similar zinc chloride loadings, the catalyst solutions made in trans-2-pentenenitrile solutions react faster with 2-methyl-3-butenenitrile than catalyst solutions made in 3-pentenenitrile solutions.

EXAMPLES

Nine samples of catalyst were prepared under the conditions described, then each was tested for its ability to carry out the 2-methyl-3-butenenitrile isomerization to pentenenitriles.

Example 1: Catalyst Preparation: (V) Ligand Solution with 3-pentenitrile and $ZnCl_2$ In a nitrogen glove-box, nickel metal, 0.40 g, (V) ligand solution, 1.05 g, $ZnCl_2$, 0.05 g, and 3-pentenenitrile, 3.90 g were combined in a 10 ml serum bottle sealed with a Teflon lined septum. The solution was stirred with a magnetic stirrer at 65° C. for 24 hours to obtain a nickel catalyst solution. The amount of nickel in solution was measured by high-performance liquid chromatography (HPLC) after pre-treating with excess tris(biphenol)diphosphite and heat to stabilize the nickel complex during the analysis by HPLC, Table 2.

Example 2: Catalyst Preparation: (V) Ligand Solution with 3-pentenitrile

In a nitrogen glove-box, nickel metal, 0.40 g, (V) ligand solution, 1.05 g, and 3-pentenitrile, 3.95 g were combined in a 10 ml serum bottle sealed with a Teflon lined septum. The solution was stirred with a magnetic stirrer at 65° C. for 24 hours to obtain a nickel catalyst solution. The amount of nickel in solution was measured by high-performance liquid chromatography after pre-treating with excess tris(biphenol) diphosphite and heat to stabilize the nickel complex during the analysis by HPLC, Table 2.

Example 3: Catalyst Preparation: (V) Ligand Solution with cis-2-pentenitrile

In a nitrogen glove-box, nickel metal, 0.40 g, (V) ligand solution, 1.05 g, and cis-2-pentenitrile, 3.95 g were combined in a 10 ml serum bottle sealed with a Teflon lined septum. The solution was stirred with a magnetic stirrer at 65° C. for 24 hours to obtain a nickel catalyst solution. The amount of nickel in solution was measured by high-performance liquid chromatography (HPLC) after pre-treating with excess tris(biphenol)diphosphite and heat to stabilize the nickel complex during the analysis by HPLC, Table 2.

Example 4: Catalyst Preparation: (V) Ligand Solution with trans-2-pentenitrile and Zinc Chloride In a nitrogen glove-box, nickel metal, 0.40 g, (V) ligand solution, 1.05 g, zinc chloride, 0.05 g, and trans-2-pentenenitrile, 3.95 g and were combined in a 10 ml serum bottle sealed with a Teflon lined septum. The solution was stirred with a magnetic stirrer at 65° C. for 24 hours to obtain a nickel catalyst solution. The amount of nickel in solution was measured by high-performance liquid chromatography (HPLC) after pre-treating with excess tris(biphenol)diphosphite and heat to stabilize the nickel complex during the analysis by HPLC, Table 2.

Example 5: Catalyst Preparation: (V) Ligand Solution with trans-2-pentenitrile

In a nitrogen glove-box, nickel metal, 0.40 g, (V) ligand solution, 1.05 g, and trans-2-pentenenitrile, 3.95 g were combined in a 10 ml serum bottle sealed with a Teflon lined septum. The solution was stirred with a magnetic stirrer at 65° C. for 24 hours to obtain a nickel catalyst solution. The amount of nickel in solution was measured by high-performance liquid chromatography (HPLC) after pre-treating with excess tris(biphenol)diphosphite and heat to stabilize the nickel complex during the analysis by HPLC, Table 2.

Example 6: Catalyst Preparation: (XIII) Ligand Solution with trans-2-Pentenitrile and Zinc Chloride In a nitrogen glove-box, nickel metal, 0.40 g, (XIII) ligand solution, 1.05 g, zinc chloride, 0.05 g, and trans-2-pentenenitrile, 3.95 g were combined in a 10 ml serum bottle sealed with a Teflon lined septum. The solution was stirred with a magnetic stirrer at 65° C. for 24 hours to obtain a nickel catalyst solution. The amount of nickel in solution was measured by high-performance liquid chromatography (HPLC) after pre-treating with excess tris(biphenol)diphosphite and heat to stabilize the nickel complex during the analysis by HPLC, Table 2.

Example 7: Catalyst Preparation: (XIII) Ligand Solution with trans-2-pentenitrile In a nitrogen glove-box, nickel metal, 0.40 g, (XIII) ligand solution, 1.05 g, and trans-2-pentenenitrile, 3.95 g were combined in a 10 ml serum bottle sealed with a Teflon lined septum. The solution was stirred with a magnetic stirrer at 65° C. for 24 hours to obtain a nickel catalyst solution. The amount of nickel in solution was measured by high-performance liquid chromatography (HPLC) after pre-treating with excess tris(biphenol)diphosphite and heat to stabilize the nickel complex during the analysis by HPLC, Table 2.

Example 8: Catalyst Preparation: (XIII) Ligand Solution with 3-pentenitrile and Zinc Chloride In a nitrogen glove-box, nickel metal, 0.40 g, (XIII) ligand solution, 1.05 g, zinc chloride, 0.05 g, and 3-pentenenitrile, 3.95 g were combined in a 10 ml serum bottle sealed with a Teflon lined septum. The solution was stirred with a magnetic stirrer at 65° C. for 24 hours to obtain a nickel catalyst solution. The amount of nickel in solution was measured by high-performance liquid chromatography (HPLC) after pre-treating with excess tris(biphenol)diphosphite and heat to stabilize the nickel complex during the analysis by HPLC, Table 2.

Example 9: Catalyst Preparation: (XIII) Ligand Solution with 3-pentenitrile

In a nitrogen glove-box, nickel metal, 0.40 g, (XIII) ligand solution, 1.05 g, and 3-pentenenitrile, 3.95 g were combined in a 10 ml serum bottle sealed with a Teflon lined septum. The solution was stirred with a magnetic stirrer at 65° C. for 24 hours to obtain a nickel catalyst solution. The amount of nickel in solution was measured by high-performance liquid chromatography (HPLC) after pre-treating with excess tris(biphenol)diphosphite and heat to stabilize the nickel complex during the analysis by HPLC, Table 2.

Example 10: Isomerization of 2-methyl-3-butenenitrile

A portion of nickel catalyst containing solution from Example 1-, 0.50 g, was filtered from the remaining nickel metal and was combined with 5.00 g of 2-methyl-3-butenenitrile. The solution was heated to 100° C. for 5 hours and then cooled to room temperature within 5 minutes and analyzed for conversion of 2-methyl-3-butenenitrile by GC. The resulting 2-methyl-3-butenenitrile conversion after 5 hours is listed in the table 3. Same procedure was used with nickel catalyst containing solutions from examples 2-9.

All patents and publications referred to herein are incorporated by reference herein to the same extent as if each individual publication was specifically and individually indicated to be incorporated by reference in its entirety.

The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

What is claimed is:

1. A process for hydrocyanation of butadiene to adiponitrile, the process comprising:
   hydrocyanating butadiene to form adiponitrile, the hydrocyanating comprising contacting 2-methyl-3-butenenitrile and a hydrocyanation catalyst system in a solvent system consisting essentially of cis-2-pentenenitrile, trans-2-pentenenitrile, or a mixture thereof, in the absence of a Lewis acid promoter, wherein an unwanted byproduct of the hydrocyanating of the 2-methyl-3-butenenitrile is converted in situ to a process intermediate pentenenitrile that undergoes further hydrocyanation to provide the adiponitrile, the hydrocyanation catalyst system comprising a soluble complex of nickel and a bidentate ligand of formula (III),

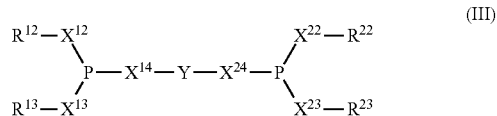

wherein $X^{12}$, $X^{13}$, $X^{14}$, $X^{22}$, $X^{23}$, and $X^{24}$ each independently is oxygen;

wherein $R^{12}$, $R^{13}$, $R^{22}$, and $R^{23}$, each independently is (C1-C10)alkyl, (C3-C10)cycloalkyl, (C3-C10)cycloalkyl(C1-C10)alkyl, (C6-C20)aryl, or (C6-C20)aryl(C1-C10)alkyl, wherein for any (C6-C20)aryl or (C6-C20)aryl(C1-C10)alkyl of $R^{12}$, $R^{13}$, $R^{22}$, or $R^{23}$, each aryl ring thereof is unsubstituted or is substituted with 1-4 substituents independently selected from the group consisting of (C1-C10)alkyl, (C3-C10)cyclo alkyl, (C1-C10)alkoxy, (C3-C10)cyclo alkoxy, (C3-C10)cycloalkyl(C1-C10)alkyl, (C3-C10)cycloalkoxy(C1-C10)alkyl, (C3-C10)cycloalkyl(C1-C10)alkoxy, (C3-C10)cycloalkoxy(C1-C10)alkoxy, (C6-C20)aryl, and (C6-C20)aryl(C1-C10)alkyl; or, optionally, one or more of pairs $R^{12}$ and $R^{13}$ or $R^{22}$ and $R^{23}$ are mutually directly bonded, such that the $R^{12}X^{12}$ and $R^{13}X^{13}$ groups, or the $R^{22}X^{22}$ and $R^{23}X^{23}$ groups, or both, together with the respective phosphorus atom to which each pair of groups is bonded, forms a respective ring; and Y is an (C6-C20)arylene group, wherein each ring thereof is independently unsubstituted or is substituted with 1-4 (C1-C10)alkyl, (C3-C10)cycloalkyl, (C1-C10)alkoxy, (C3-C10)cycloalkoxy, (C3-C10)cycloalkyl(C1-C10)alkyl, (C3-C10)cycloalkoxy(C1-C10)alkyl, (C3-C10)cycloalkyl(C1-C10)alkoxy, (C3-C10)cycloalkoxy(C1-C10)alkoxy, (C6-C20)aryl, (C6-C20)aryl(C1-C10)alkyl, fluorine, chlorine, bromine, or (C1-C10)haloalkyl.

2. The process of claim 1, wherein the solvent system consists essentially of cis-2-pentenenitrile.

3. The process of claim 1, wherein the bidentate ligand is present in a ratio of 1:4 by weight relative to the solvent system.

4. The process of claim 1 wherein the bidentate ligand is of formula (XII)

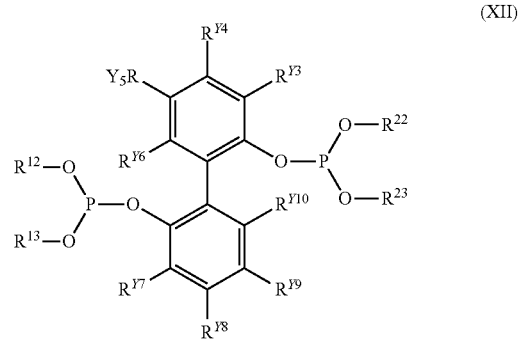

wherein $R^{12}$, $R^{13}$, $R^{22}$ and $R^{23}$ are each independently an unsubstituted or a substituted monovalent aryl, and each of $R^{Y3}$-$R^{Y10}$ is independently selected from the group consisting of hydrogen, (C1-C10) alkyl, and (C1-C10)alkoxy, or wherein two adjacent $R^{Y3}$-$R^{Y10}$ groups together form an optionally substituted fused aryl ring.

5. The process of claim 4 wherein $R^{12}$, $R^{13}$, $R^{22}$, and $R^{23}$ are each independently phenyl substituted at a respective single ortho-position with a (C1-C10)alkyl or (C1-C10) alkoxy, wherein respective meta- and para-positions of the $R^{12}$, $R^{13}$, $R^{22}$, and $R^{23}$ phenyls can each independently be unsubstituted or be independently substituted with (C1-C10) alkyl, (C3-C10)cycloalkyl, (C1-C10)alkoxy, (C3-C10)cycloalkoxy, (C3-C10)cycloalkyl(C1-C10)alkyl, (C3-C10)cycloalkoxy(C1-C10)alkyl, (C3-C10)cycloalkyl(C1-C10)alkoxy, or (C3-C10)cyclo alkoxy(C1-C10)alkoxy;

$R^{Y6}$ and $R^{Y10}$ are independently (C1-C10)alkyl or (C1-C10)alkoxy, and $R^{Y3}$, $R^{Y4}$, $R^{Y5}$, $R^{Y7}$, $R^{Y8}$, and $R^{Y9}$, are independently H, (C1-C10)alkyl, or (C1-C10)alkoxy, provided that at least one of $R^{Y3}$, $R^{Y4}$, or $R^{Y5}$, and at least one of $R^{Y7}$, $R^{Y8}$, or $R^{Y9}$, is (C1-C10)alkyl or (C1-C10)alkoxy.

6. The process of claim 1, wherein the bidentate ligand is of formula (V):

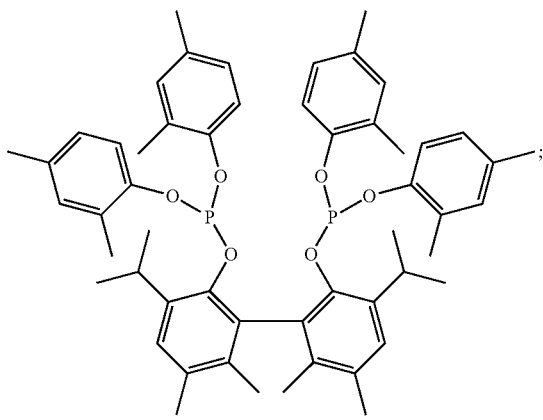

(V)

or is of formula (XIII):

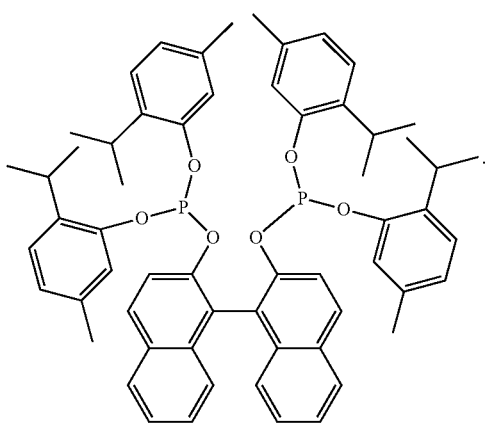

(XIII)

7. The process of claim 1, wherein the catalyst system is free of $ZnCl_2$.

8. The process of claim 1, wherein the solvent system consists essentially of cis-2-pentenenitrile.

9. The process of claim 1, wherein the bidentate ligand is present in a ratio of 1:4 by weight relative to the solvent system.

10. The process of claim 1, wherein the contacting is performed in the presence of hydrogen cyanide.

11. The process of claim 1, wherein the contacting is performed at a temperature of 80° C. to 140° C.

12. The process of claim 1, wherein the contacting is performed at a temperature of 100° C. to 130° C.

13. The process of claim 1, further comprising preparing the hydrocyanation catalyst system, comprising:
contacting nickel metal and the bidentate ligand of formula (III) in an organic solvent system consisting essentially of cis-2-pentenenitrile, trans-2-pentenenitrile, or a mixture thereof, under conditions suitable to bring about reaction of the bidentate ligand and the nickel metal to provide an effective concentration of the nickel-ligand complex dissolved in the organic solvent system.

14. The process of claim 13, wherein the conditions to bring about reaction of the bidentate ligand and the nickel metal comprise a temperature of 25-75° C.

15. The process of claim 14, wherein the conditions to bring about reaction of the bidentate ligand and the nickel metal comprise a temperature of 65° C.

* * * * *